United States Patent [19]
Ellinwood et al.

[11] Patent Number: 5,354,780
[45] Date of Patent: Oct. 11, 1994

[54] INTRAORAL DOSING METHOD OF ADMINISTERING (+)-α-4-(DIMETHYLAMINO)-3-METHYL-1,2-DIPHENYL-2-BUTANOLPROPIONATE

[76] Inventors: Everett H. Ellinwood, 3519 Tonbridge Way, Durham, N.C. 27707; Samir K. Gupta, 5011 S. Alston Ave., Apt. D-201, Durham, N.C. 27713

[21] Appl. No.: 38,911

[22] Filed: Mar. 29, 1993

Related U.S. Application Data

[63] Continuation-in-part of Ser. No. 703,049, May 17, 1991, Pat. No. 5,198,436, which is a continuation of Ser. No. 422,992, Oct. 17, 1989, abandoned.

[51] Int. Cl.$^5$ ............................................. A61K 31/135
[52] U.S. Cl. .................................................... 514/649
[58] Field of Search ................ 514/646, 649; 424/464, 424/435

[56] References Cited

U.S. PATENT DOCUMENTS

| | | | |
|---|---|---|---|
| 2,728,779 | 12/1955 | Pohland et al. | 548/573 |
| 3,972,995 | 8/1976 | Tsuk et al. | 424/28 |
| 5,198,436 | 3/1993 | Ellinwood, Jr. et al. | 514/221 |

*Primary Examiner*—Marianne M. Cintins
*Assistant Examiner*—T. J. Criares
*Attorney, Agent, or Firm*—Richard E. Jenkins

[57] ABSTRACT

A method of therapeutically administering certain $BZ_1$ specific trifluorobenzodiazepines in order to maximize the $BZ_1$ effects and minimize the $BZ_2$ effects on the human central nervous system in order to maximize the anti-anxiety, anticonvulsant and hypnotic effects and minimize the ataxic and incoordination effects of the drug. Also, a method of sublingual administration of trifluorobenzodiazepines and certain other compounds in order to decrease unwanted dealkylated metabolites.

1 Claim, 8 Drawing Sheets

Figure 1. Sublingual VS Oral Q and DOQ, Single Dosing

Figure 2. Sublingual VS Oral Q and DOQ, Single Dosing

Figure 4. Sublingual VS Oral HZ and NDZ, Single Dosing

INTRAORAL DOSING METHOD OF ADMINISTERING (+)-α-4-(DIMETHYLAMINO)-3-METHYL-1,2-DIPHENYL-2-BUTANOLPROPIONATE

RELATED APPLICATIONS

This application is a continuation-in-part application of Ser. No. 07/703,049 filed May 17, 1991, and now U.S. Pat. No. 5,198,436, which is a continuation application of Ser. No. 07/422,992 filed Oct. 17, 1989, and now abandoned.

TECHNICAL FIELD

This invention relates to a novel method of administering certain benzodiazepines which surprisingly results in a maximization of the effect on $BZ_1$ receptors and minimization of the effect on $BZ_2$ receptors of the human central nervous system so as to maximize the antianxiety, anticonvulsant, and/or hypnotic effects and to minimize the ataxic and incoordination effects of the drug thereon.

BACKGROUND ART

The most pertinent prior art reference known to applicants is U.S. Pat. No. 4,229,447 to Porter which discloses a method of administering certain benzodiazepines sublingually and buccally. Porter specifically mentions the sublingual or buccal administration of diazepam, lorazepam, oxazepam, temazepam and chlorodiazepoxide and describes two generic structures of benzodiazepines that may be administered sublingually or buccally. The compound shown below is contemplated by the generic structures in Porter. All of the benzodiazepines disclosed and the generic structure described in Porter are $BZ_1$-$BZ_2$ receptor non-specific since they lack the trifluoro ethyl group in the N position of the "B" ring which confers $BZ_1$ specificity.

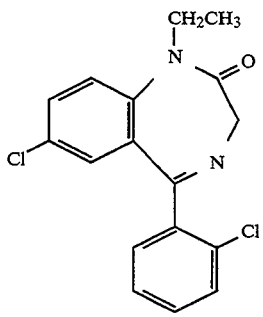

Porter's method is based on the rapid buccal or sublingual absorption of selected benzodiazepines to attain effective plasma concentration more rapidly than oral administration. In contrast, while parenteral administration provides a rapid rise of blood levels of the benzodiazepines, parenteral administration is frequently accompanied by pain and irritation at the injection site and may require sterilization of the preparatives and the hypodermic syringes.

Porter points out that the intraoral, i.e. buccal or sublingual administration, of lipid soluble benzodiazepines results in therapeutic levels resembling parenteral administration without some of the problems associated therewith. Porter's administration technique for benzodiazepines in general builds on a long established knowledge in pharmacology that drugs absorbed in the intraoral route give rise to more rapid absorption than when swallowed into the stomach. What is not recognized by Porter, however, are concerns with first-pass metabolism which can be avoided either with the sublingual or parenteral route of drug administration of certain benzodiazepines.

Porter does not recognize that first-pass metabolism designates the drug absorption directly into the portal blood supply leading to the liver and that the liver in turn rapidly absorbs and metabolizes the drug with its first-pass high concentration through the liver blood supply. Thus, large amounts of the drug may never be seen by the systemic circulation or drug effect site. Porter further does not recognize that the more rapid metabolism via the first-pass metabolism route can lead to accelerated dealkylation with formation of high plasma concentrations of an unwanted metabolite. Thus, applicants' concern with avoiding the degradation of the parent compound and its desired positive effect and the metabolism thereof to an undesired metabolite is neither recognized nor addressed by Porter, which only addresses the ability of the oral mucous membranes to absorb certain benzodiazepines fast and achieve high plasma levels thereof quickly.

The specific drug for which this phenomenon was demonstrated by Porter was lorazepam which has a simple metabolism that results in it not being metabolized to active compounds. Also, and very significantly, the issue of human nervous system receptor specificity and activation for $BZ_1$ and $BZ_2$ type receptors is not recognized by Porter either generally or with reference specifically to trifluorobenzodiazepines.

U.S. Pat. No. 3,694,552 to Hester discloses that 3-(5-phenyl-3H-1,4-benzodiazepine-2-yl) carbazic acid alkyl esters, which are useful as sedatives, hypnotics, tranquilizers, muscle relaxants and anticonvulsants, can be administered sublingually. Subsequently issued U.S. Pat. No. 4,444,781 to Hester specifically teaches that 8-chloro-1-methanol-6-(o-chlorophenyl)-4H-s-triazolo[4,3-a][1,4]-benzodiazepine therapeutic compounds, which are useful as soporifics, can be suitably prepared for sublingual use.

Also, U.S. Pat. No. 4,009,271 to vonBebenburg et al. discloses that 6-aza-3H-1,4-benzodiazepines and 6-aza-1,2-dihydro-3H-1,4-benzodiazepines (which have pharmacodynamic properties including psychosedative and anxiolytic properties as well as antiphlogistic properties) can be administered enterally, parenterally, orally or perlingually.

DISCLOSURE OF THE INVENTION

It is well known by those practiced in the art that special distribution of enzymatic activity within the liver leads to a metabolic zonation for metabolisms of drugs. This zonation is noted in peripheral midzonal and pericentral regions of the liver. Thus, the relative distribution of 2 or more enzymes with respect to substrate entry point and the relative magnitudes of the enzymatic parameters will have a large impact on the metabolic pathway emphasized.

When a drug is swallowed, the stomach and small intestine absorb it with subsequent flow to the portal vein entry to the liver. Thus differential metabolic zonation is possible if the drug is distributed to the liver by the portal vein rather than by the hepatic artery from the general circulation.

Even though this general background information is known to those practiced in the art, the specific findings that trifluorobenzodiazepine N-desalkylation is reduced by sublingual/buccal administration was not known until applicants' unexpected discovery with quazepam and halazepam.

In accordance with the present invention, applicants provide a novel method for maximizing the effect of selected trifluorobenzodiazepines including 7-chloro-1-(2,2,2-trifluoroethyl)-5-(o-fluorophenyl)-1,3-dihydro-2H-1,4-benzodiazepine-2-thione (quazepam) and 7-chloro-1,3 dihydro-5-phenyl-1-1-(2,2,2-trifluoroethyl)-2H-1,4-benzodiazepine-2-one (halazepam) on benzodiazepine Type I ($BZ_1$) receptors and minimizing the unwanted potent effect of certain metabolites on benzodiazepine Type II ($BZ_2$) receptors of the human central nervous system so as to maximize the antianxiety and anticonvulsant and/or hypnotic effects and minimize the ataxic and incoordination effects thereon, comprising selecting a suitable lipid soluble and $BZ_1$ specific trifluoro-benzodiazepine, placing the trifluorobenzodiazepine in a suitable intraoral formulation, and intraorally administering a therapeutically effective amount of said intraoral formulation so as to bypass the first pass metabolism of said selected trifluorobenzodiazepine in the liver. The selected trifluorobenzodiazepines with $BZ_1$ specificity are represented by the following structural formula and include:

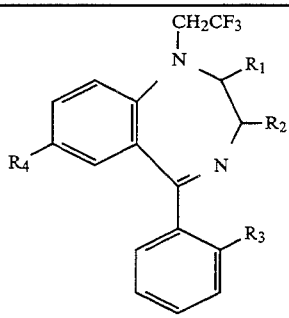

| COMPOUND | $R_1$ | $R_2$ | $R_3$ | $R_4$ |
|---|---|---|---|---|
| 1. HALAZEPAM | =O | H,H | H | Cl |
| 2. 3-OH-HALAZEPAM | =O | OH,H | H | Cl |
| 3. QUAZEPAM (Q) | =S | H,H | F | Cl |
| 4. 2-OXO-Q | =O | H,H | F | Cl |
| 5. 2-OXO-3-OH-Q | =O | OH,H | F | Cl |
| 6. SCH 15698 | H,H | H,H | F | Cl |
| 7. SCH 16893 | H,H | H,H | Cl | Cl |
| 8. SCH 18449 | H,H | H,H | F | Br |
| 9. 3-OH-Q | =S | OH,H | F | Cl |

1. 7-chloro-1-(2,2,2-trifluoroethyl)-5-phenyl-1,3-dihydro-2H-1,4-benzodiazepin-2-one.
2. 7-chloro-1-(2,2,2-trifluoroethyl)-5-phenyl-1,3-dihydro-3-hydroxy-2H-1,3-benzodiazepin-2-one.
3. 7-chloro-1-(2,2,2-trifluoroethyl)-5-(2-fluorophenyl)-1,3-dihydro-2H-1,4-benzodiazepin-2-thione.
4. 7-chloro-1-(2,2,2-trifluoroethyl)-5-(2-fluorophenyl)-1,3-dihydro-2H-1,4-benzodiazepin-2-one.
5. 7-chloro-1-(2,2,2-trifluoroethyl)-5-(2-fluorophenyl)-1,3-dihydro-3-hydroxy-2H-1,4-benzodiazepin-2-one.
6. 7-chloro-1-(2,2,2-trifluoroethyl)-5-(2-fluorophenyl)-1,3-dihydro-2H-1,4-benzodiazepin.
7. 7-chloro-1-(2,2,2-trifluoroethyl)-5-(2-chlorophenyl)-1,3-dihydro-2H-1,4-benzodiazepin.
8. 7-bromo-1-(2,2,2-trifluoroethyl)-5-(2-fluorophenyl)-1,3-dihydro-2H-1,4-benzodiazepin.
9. 7-chloro-1-(2,2,2-trifluoroethyl)-5-(2-fluorophenyl)-1,3-dihydro-3-hydroxy-2H-1,4-benzodiazepin-2-thione.

The trifluorobenzodiazepines referenced above are also lipid soluble. All of the benzodiazepines reported to have $BZ_1$ specificity have a $CH_2CF_3$ group on the nitrogen in the "B" ring. Metabolic loss of this $CH_2CF_3$ group results in a benzodiazepine that is non-specific for the $BZ_1$-$BZ_2$ receptors. Applicants' invention was made possible by the unexpected and surprising discovery from pharmacokinetic studies that sublingual dosing minimizes the desalkylation metabolic pathway leading to the formation of nonspecific metabolites of the selected trifluorobenzodiazepine.

An object of the present invention is to increase the effectiveness of certain selected trifluorobenzodiazepines on human subjects to reduce anxiety and convulsions.

Another object of the present invention is to provide a new administration method which increases the availability of certain selected trifluorobenzodiazepines to the human central nervous system and decreases the amount of undesirable metabolites available thereto.

Still another object of the present invention is to maximize the effect of certain selected trifluorobenzodiazepines on $BZ_1$ receptors of the human central nervous system and minimize their effect on $BZ_2$ receptors.

BEST MODE FOR CARRYING OUT THE INVENTION

Quazepam, a trifluorobenzodiazepine, is selective for benzodiazepine Type I ($BZ_1$) receptors of the central human nervous system. Action at the $BZ_1$ receptors has been linked to antianxiety and anticonvulsant and/or hypnotic effects, whereas action at $BZ_2$ receptors of the human central nervous system has been linked to muscle relaxation and ataxic effects. N-desalkyl-2-oxoquazepam (DOQ), an active metabolite of quazepam (Q), is $BZ_1$, $BZ_2$ receptor non-specific, and also has a much higher affinity or potency for both receptor types when compared to the $BZ_1$ specific affinity of quazepam (Q). Thus, the higher affinity metabolite (DOQ) of quazepam (Q) contributes substantially to the adverse ataxic and incoordination effects of quazepam on the human central nervous system. In addition, because DOQ has a much longer elimination half-life than the parent quazepam compound (Q), repeated dosing leads to the gradual accumulation of the non-specific, unwanted metabolite, and a greater ratio of DOQ/Q attains over a period of days. Thus, after two to three hours subsequent to an acute dose of quazepam, the DOQ metabolite, both because of its increased gradual accumulation and its greater potency than the parent compound Q, can obviate the advantages of quazepam itself.

Figure 1:
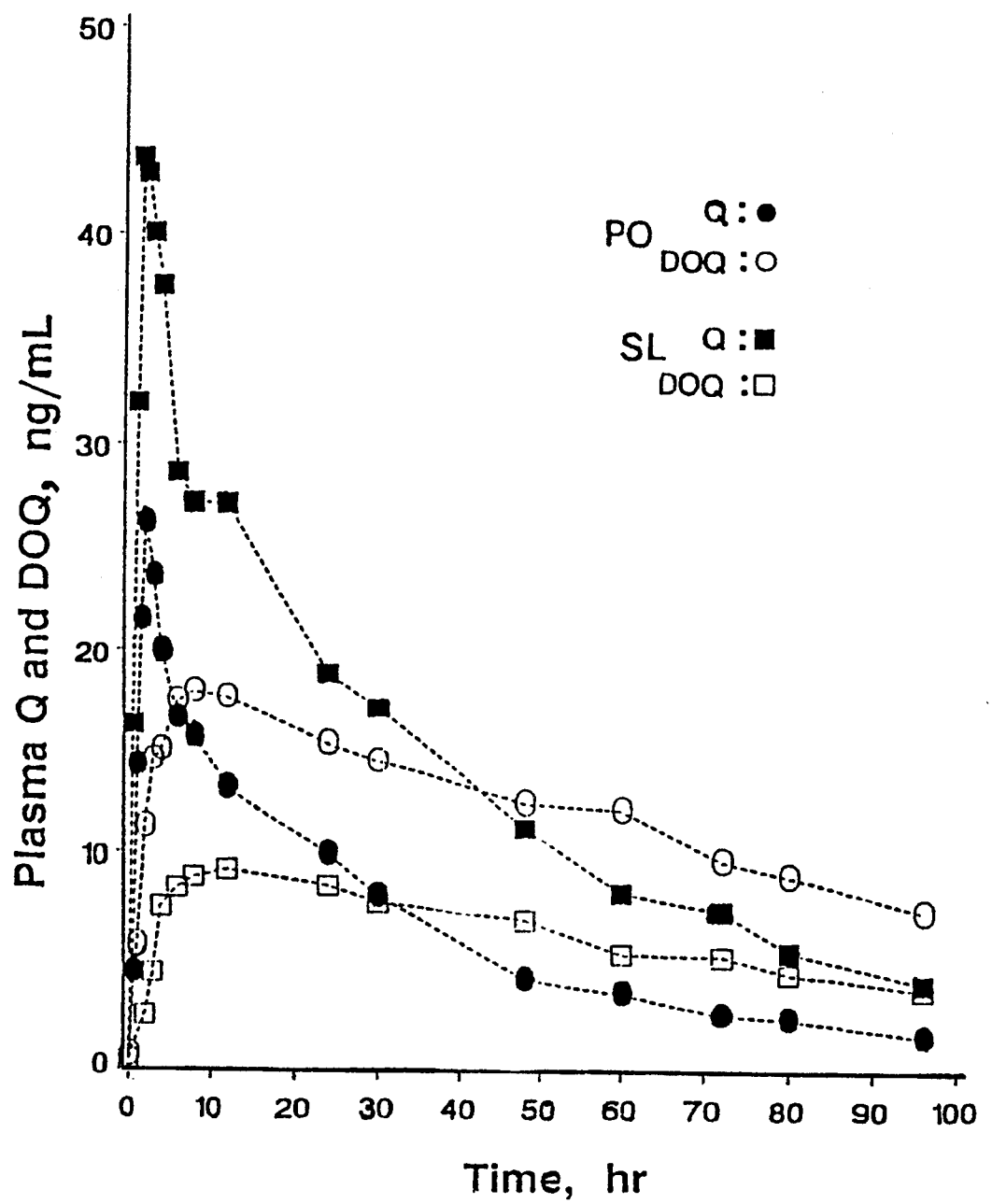
FIG. 1 is a graph illustrating the concentration of quazepam (Q) and N-desalkyl-2-oxoquazepam (DOQ) in the blood plasma over 96 hours following a single sublingual dose (SL) or per oral swallowed dose (PO) of 15 mg of quazepam.
Figure 2:
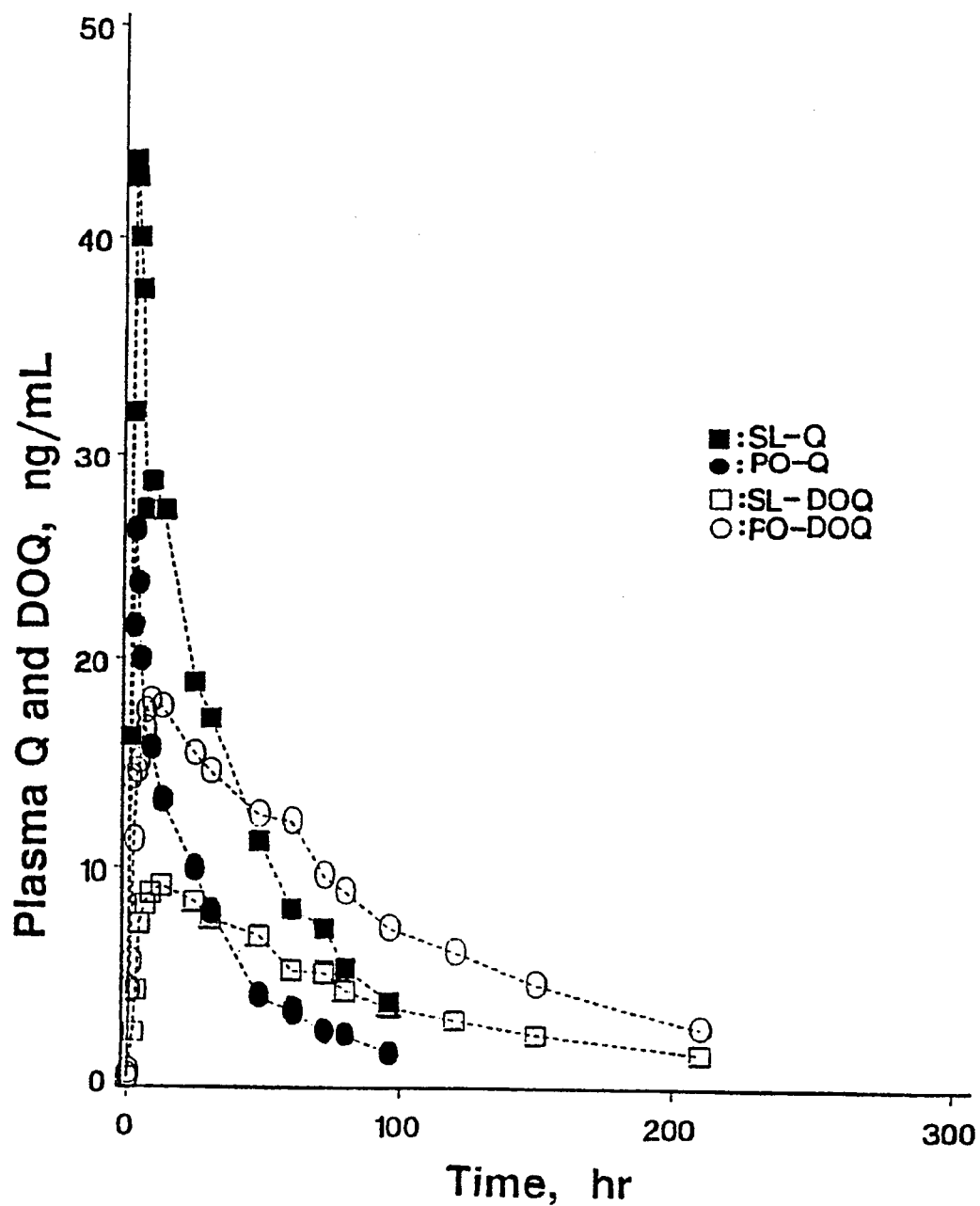
FIG. 2 is a graph illustrating the concentration of quazepam (Q) and N-desalkyl-2-oxoquazepam (DOQ) in the blood plasma over 210 hours following a single sublingual dose (SL) of 15 mg of quazepam or per oral swallowed dose (PO)
Figure 3:
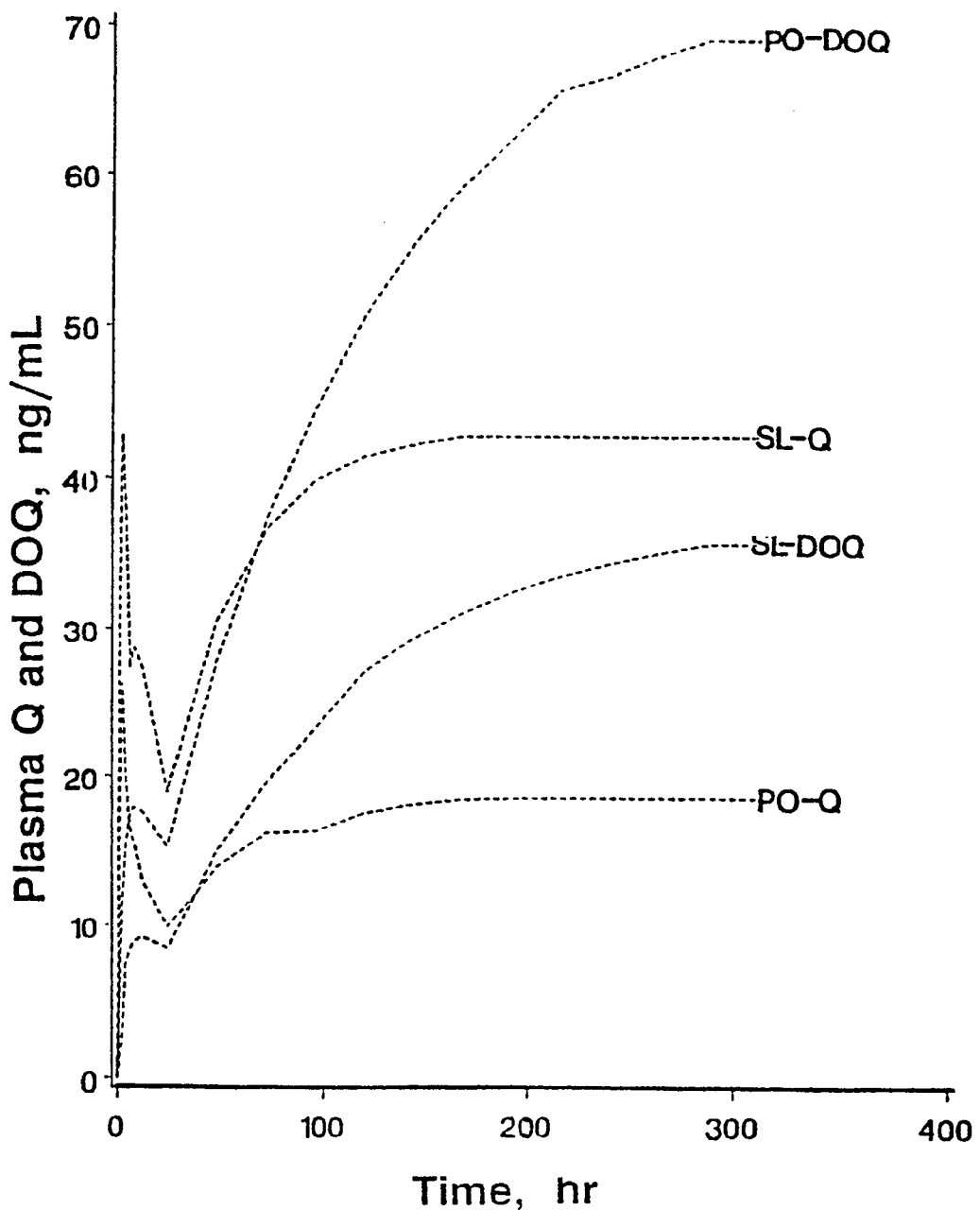
FIG. 3 is a graph of computer simulated concentration levels of quazepam and N-desalkyl-2-oxoquazepam in the blood following sublingual and oral swallowed doses of 15 mg of quazepam once a day for a 15 day period illustrating the marked reduction in accumulated levels of desalkyloxoquazepam with sublingual dosing.

Applicants have unexpectedly and surprisingly discovered that sublingual dosing, in contrast to the usual clinical oral dosing of quazepam, increases the availability of quazepam about 60% while the DOQ drops to about one-half that of the oral quazepam administration levels. In other words, applicants have unexpectedly and surprisingly discovered that the aforementioned undesirable "first pass" augmentation of dealkylation to the DOQ metabolite can be markedly reduced or obviated by sublingual dosing of quazepam. This change in concentrations for the two compounds can be seen with reference to FIG. 1 and FIG. 2 of the drawings where the differences in the parent compound Q and the metabolite DOQ for both the oral and sublingual dosing is shown. In FIG. 3, by use of standard multiple Q dose simulations, the differences in accumulation of Q and DOQ for sublingual versus oral dosing over 15 days is shown. With chronic dosing it is readily apparent that after 15 days the DOQ level, following oral administration, has reached levels that are associated with the threshold for impairing ataxic and incoordination affects (especially if larger doses are given). With sublingual dosing the accumulated levels of DOQ are approximately one-half of the oral dosing and the levels of Q are over twice that of the oral levels.

In Table 1 and Table 2, set forth below, the average pharmacokinetic parameters for both Q and DOQ for both oral and sublingual routes of administration are set forth:

TABLE I
AVERAGE PHARMACOKINETIC PARAMETERS OF QUAZEPAM FOLLOWING SUBLINGUAL AND ORAL ADMINISTRATION OF QUAZEPAM (15 mg)

| Parameter | Route of Administration of Quazepam | |
| --- | --- | --- |
|  | Sublingual | Oral |
| $t_{\frac{1}{2}}$ Ka (hr) | $0.27 \pm 0.10^a$ | $0.77 \pm 0.23$ |
| $t_{\frac{1}{2}}\lambda$ 1 (hr) | $1.44 \pm 0.45$ | $1.73 \pm 0.65$ |
| $t_{\frac{1}{2}}\lambda$ 2 (hr) | $27.72 \pm 7.18$ | $24.63 \pm 8.35$ |
| Lag time (hr)$^b$ | $0.18 \pm 0.05$ | $0.52 \pm 0.28$ |
| Cmax (ng/ml)$^b$ | $42.35 \pm 10.43$ | $26.74 \pm 6.83$ |
| tmax (hr)$^b$ | $0.78 \pm 0.31$ | $2.57 \pm 1.69$ |
| AUC (ng · hr/ml)$^b$ | $1461.35 \pm 298.67$ | $472.79 \pm 238.92$ |
| CL/F (1/hr)$^b$ | $8.78 \pm 5.25$ | $37.56 \pm 16.89$ |

$^a$Mean ± SD
$^b$Differed significantly from oral dosing (P < 0.05)
Legend:
$t_{\frac{1}{2}}$ = Half-Life
$K_a$ = Absorption
$\lambda 1$ = Rapid Distribution
$\lambda 2$ = Terminal Elimination
$C_{max}$ = Peak Plasma Concentration
$t_{max}$ = Time to Cmax
AUC = Area Under Plasma Concentration-Time Curve
CL/F = Clearance

TABLE II
AVERAGE PHARMACOKINETIC PARAMETERS OF N-DESALKYL-2-OXOQUAZEPAM FOLLOWING SUBLINGUAL AND ORAL ADMINISTRATION OF QUAZEPAM (15 mg)

| Parameter | Route of Administration of Quazepam | |
| --- | --- | --- |
|  | Sublingual | Oral |
| $t_{\frac{1}{2}}$ $K_m$ (hr) | $1.07 \pm 0.31^a$ | $1.24 \pm 0.52$ |
| $t_{\frac{1}{2}}$ $\lambda 2$ (hr) | $69.30 \pm 18.62$ | $71.44 \pm 21.16$ |
| Lag time (hr) | $1.74 \pm 0.86$ | $0.66 \pm 0.32$ |
| $C_{max}$ (ng/ml)$^b$ | $8.18 \pm 2.35$ | $17.58 \pm 4.17$ |
| $t_{max}$ (hr) | $7.33 \pm 4.15$ | $6.17 \pm 3.52$ |
| AUC (ng · hr/ml)$^b$ | $949.02 \pm 365.74$ | $1966.70 \pm 410.90$ |

$^a$Mean + SD
$^b$Differed significantly from oral dosing (P < 0.05)
Legend:
$t_{\frac{1}{2}}$ = Half-Life
$K_m$ = Formation
$\lambda 2$ = Terminal Elimination
$C_{max}$ = Peak Plasma Concentration
$t_{max}$ = Time to $C_{max}$
AUC = Area Under Plasma Concentration-Time Curve The profile in FIGS. 1 and 2 of the drawings clearly shows that there is a first-pass metabolism for Q leading to the attenuated Q levels. On the basis of applicants' pharmacokinetic studies, applicants have discovered that sublingual dosing which bypasses first pass metabolism, minimizes the N-dealkylation metabolic pathway that leads to the formation of the unwanted metabolite, DOQ. This has lead applicants to the sublingual dosing method of the invention which provides for maximization of the important therapeutic effects of the drug. Thus, applicants have discovered the means by which quazepam can be administered such that one can maximize the $BZ_1$ effect and reduce the $BZ_2$ effect of its metabolite (DOQ) and thereby enhance the efficacy in use on humans of this therapeutic drug.

In summary, applicants have discovered the following:
(1) The use of sublingual dosing of quazepam to markedly reduce first pass metabolism of the quazepam structure and thereby enhance the $BZ_1$ effect of the drug; and
(2) The use of sublingual dosing to increase the $BZ_1$-$BZ_2$ ratio with acute dosing and repeated dosing over days (since the dosing regimen is reducing the DOQ levels and thus attenuating the many impairing effects of the high affinity slowly metabolized quazepam metabolite). These phenomens resulting from sublingual dosing provide for an unexpected and surprising enhancement of the efficacy and reduction of toxicity of the drug in reducing anxiety and convulsions in humans.

Figure 4:
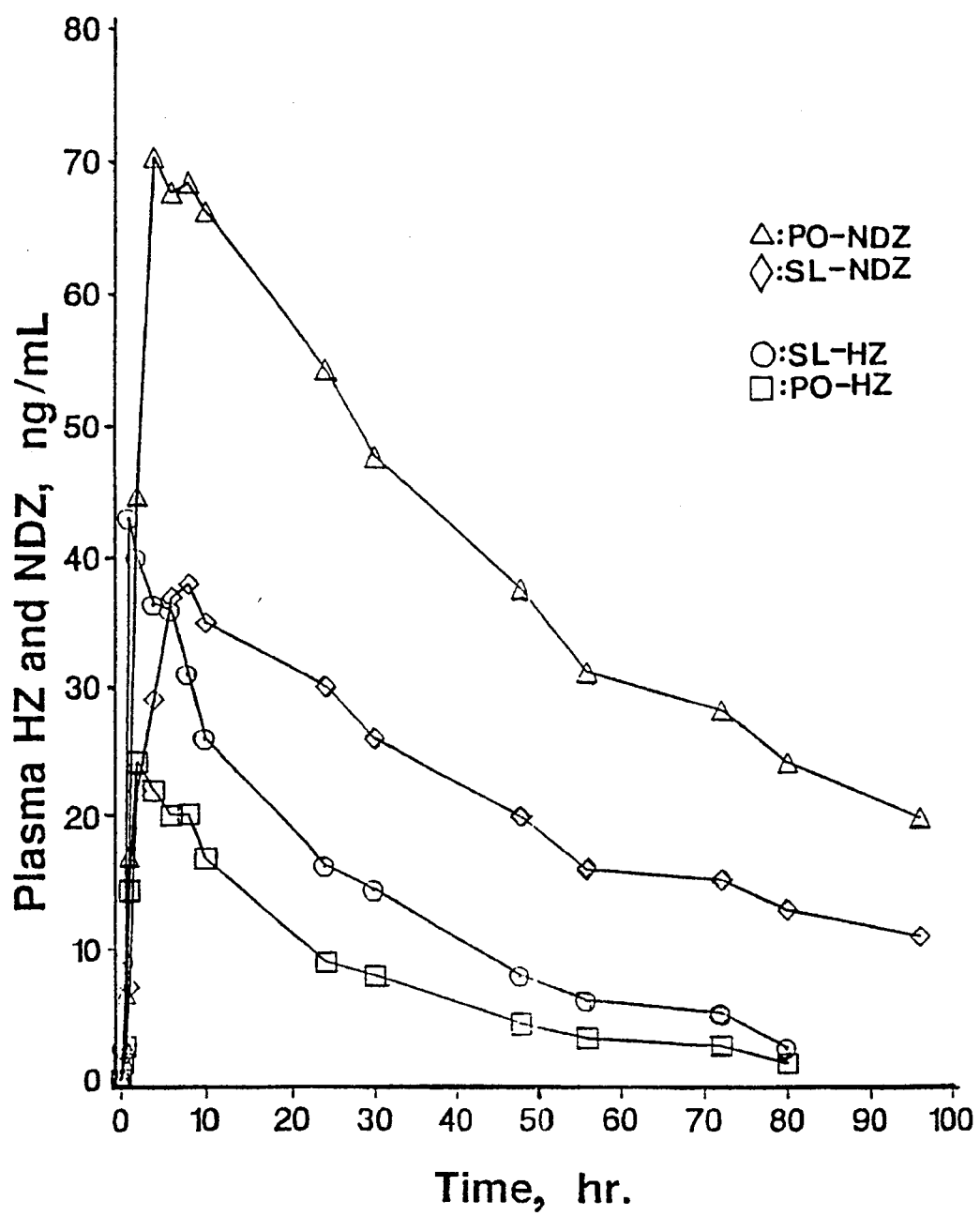
FIG. 4 is a graph illustrating the concentration of halazepam (HZ) and N-desalkyl-3-hydroxy-halazepam (ND) in the blood over 96 hours following a single sublingual dose (SL) or per oral swallowed dose (PO) of 20 mg of halazepam.
Figure 5:
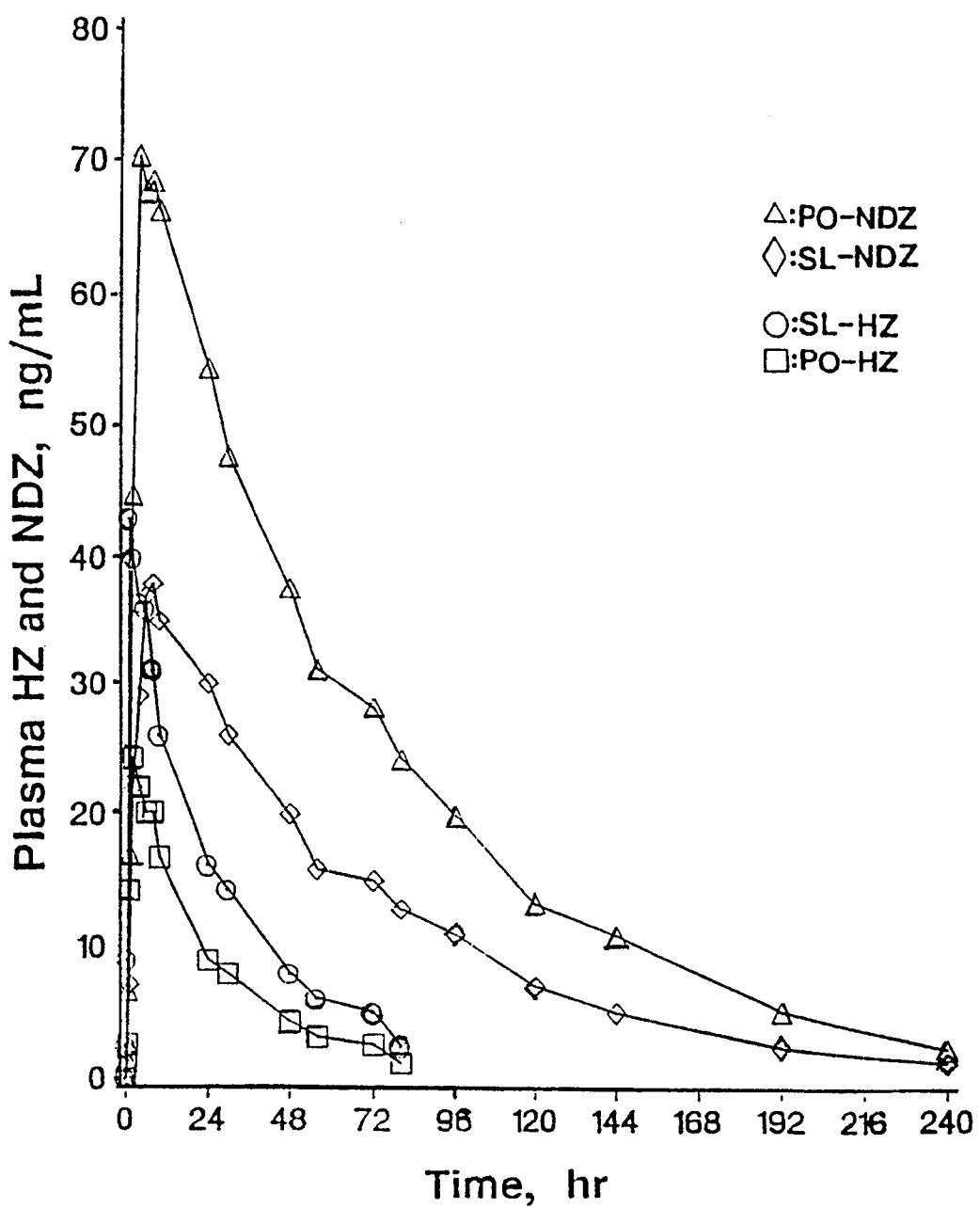
FIG. 5 is a graph illustrating the concentration of halazepam (HZ) and N-desalkyl-3-hydroxy-halazepam (ND) in the blood over 240 hours following a single sublingual dose (SL) or per oral swallowed (PO) of 20 mg of halazepam.
Figure 6:
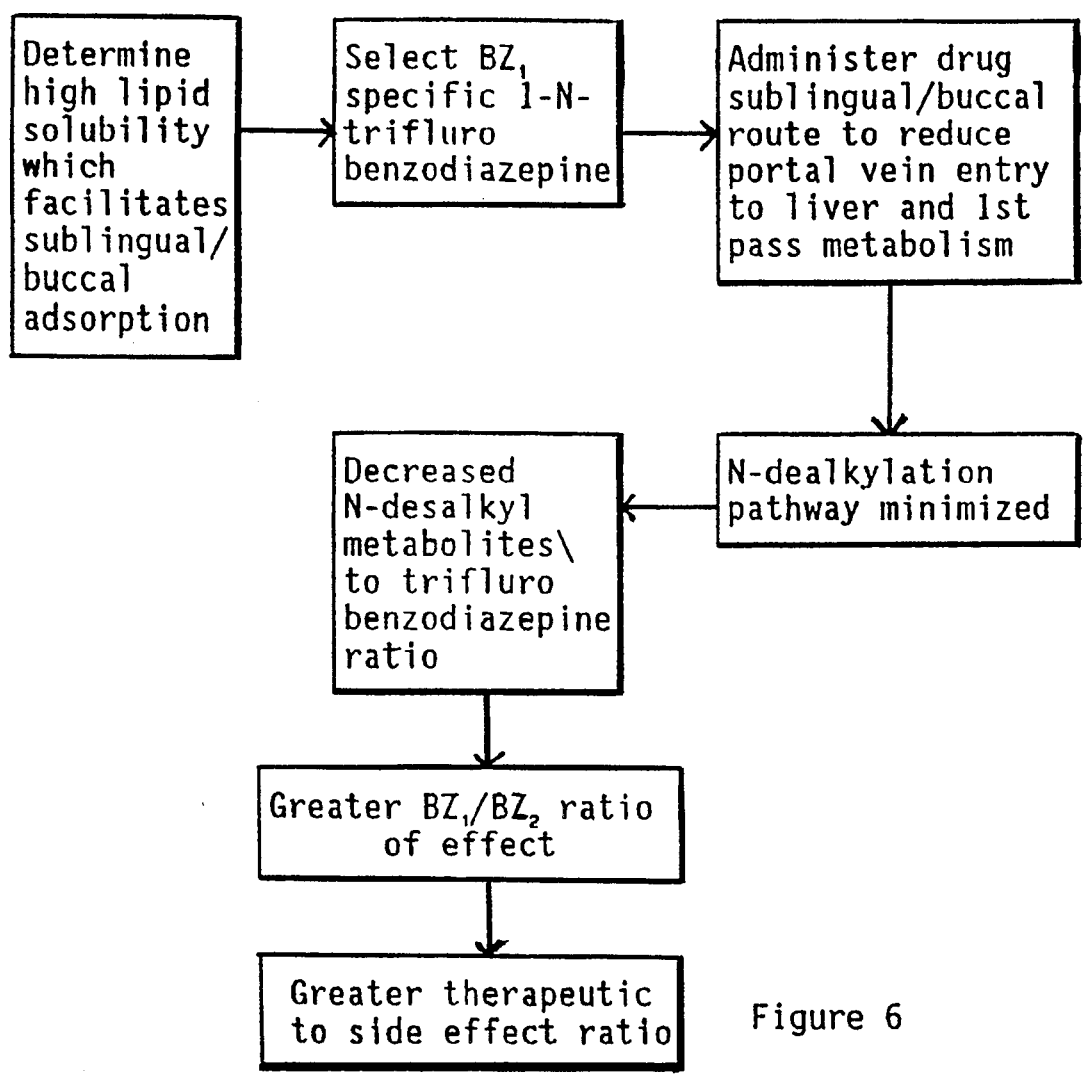
FIG. 6 is a flow chart of the method of the present invention.

With references now to FIGS. 4 and 5, applicants have also tested high $BZ_1$ specific drug halazepam and discovered similar results obtained by sublingual administration thereof: The availability of halazepam was significantly increased thus maximizing the $BZ_1$ effect while reducing the $BZ_1$-$BZ_2$ metabolite N-dealkylhydroxy-halazepam. Applicants thus believe that intraoral administration, either buccal or sublingual, of selected trifluorobenzodiazepines can substantially enhance their therapeutic effect for the reasons set forth herein. Applicants' novel method can be better appreciated with reference to FIG. 6 of the drawings which depicts a flow chart of the steps of the novel therapeutic method.

Alternative Embodiment of the Invention

Thus applicants have made the discovery of the sublingual route of administration for enhancing the $BZ_1$ specific effects of the trifluorobenzodiazepines by inhibiting the formation of unwanted metabolite.

Applicants have shown hereinabove that the manner in which the original blood borne trifluorobenzodiazepine drug enters into the liver has a profound effect on the directing of the vector of metabolism for this given species of drugs. This class of benzodiazepines has a dealkylation metabolism. Applicants' findings of the alteration of metabolism by sublingual administration led to the novel discovery that one could alter the steady state metabolic profile of this class of drugs by bypassing the profound early stage dealkylation metabolism that occurred when the swallowed drug entry was via the portal vein metabolic pathway. This discovery required projection of acute dosing pharmacokinetics to fully understand and project steady state pharmacokinetics that document the robust advantages of the sublingual administration route in: (1) shifting to a reduced dealkylation metabolic profile; (2) reducing the production of unwanted nonspecific metabolites; and (3) thereby, enhancing an advantageous ratio $BZ_1$ specific to the nonspecific $BZ_1$, $BZ_2$ metabolites.

To the original discovery described hereinabove that N-dealkylation of trifluorobenzodiazepines could be markedly reduced by sublingual administration, applicants now have discovered that dealkylation of other drugs can be reduced by sublingual or buccal administration. These other drugs also have unwanted or toxic dealkylation metabolites.

For example, propoxyphene ((+)-α-4-(dimethylamino)-3-methyl-1,2-diphenyl-2-butanol propionate hydrochloride), a widely used, prescribed, oral analgesic is frequently associated with poisonings and death. A major concern is that accumulating levels of the non-analgesic metabolite norpropoxyphene has cardiac conduction depressing effects that are a source of cardiotoxicity. The wanted analgesic effects of propoxyphene are limited by its short half life, whereas, the unwanted norpropoxyphene metabolite has a half life of 2-3 times that of the propoxyphene. With multiple dosing the norpropoxyphene metabolite half life may increase to 39 hours, thus accumulating over days of use.

Propoxyphene is N-dealkylated similarly to the trifluorobenzodiazepines. Since its dealkylated metabolite norpropoxyphene has the potential to induce cardiac conduction delay with toxic consequences at accumulated doses, applicants explored the sublingual route of administration. Two normal subjects were given 65 mg of propoxyphene both by per oral swallowed and sublingual administration.

Figure 7:
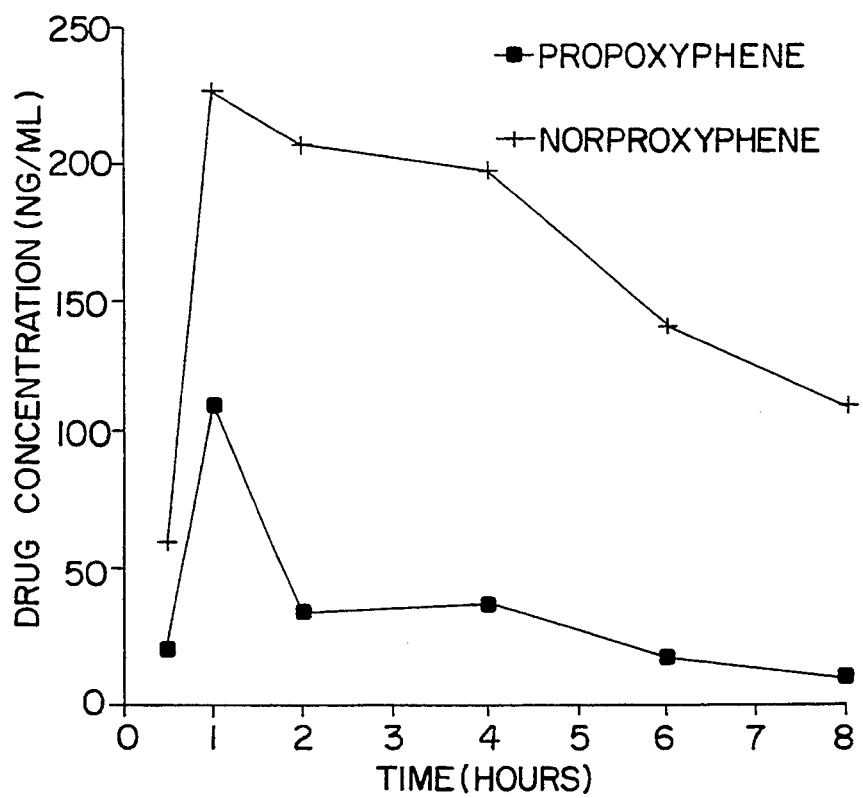
FIG. 7 is a graph illustrating the concentration of propoxyphene and norpropoxyphene in the blood plasma over 8 hours following a single per oral swallowed dose of 65 mg of propoxyphene.
Figure 8:
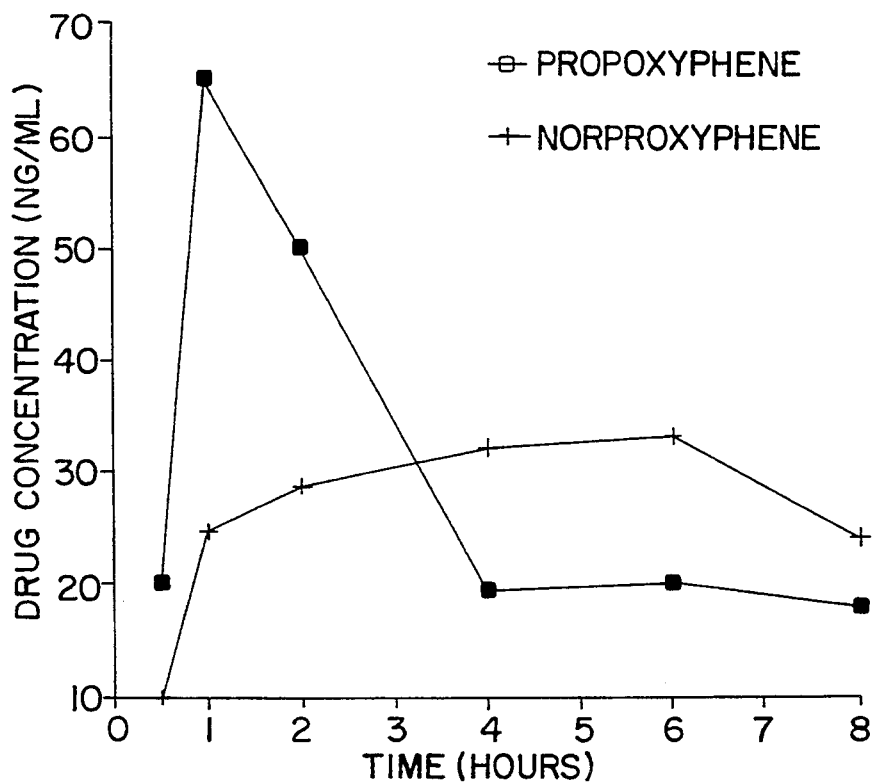
FIG. 8 is a graph illustrating the concentration of propoxyphene and norpropoxyphene in the blood plasma over 8 hours following a single sublingual dose of 65 mg of propoxyphene in the same subject as seen in FIG. 7.
Figure 9:
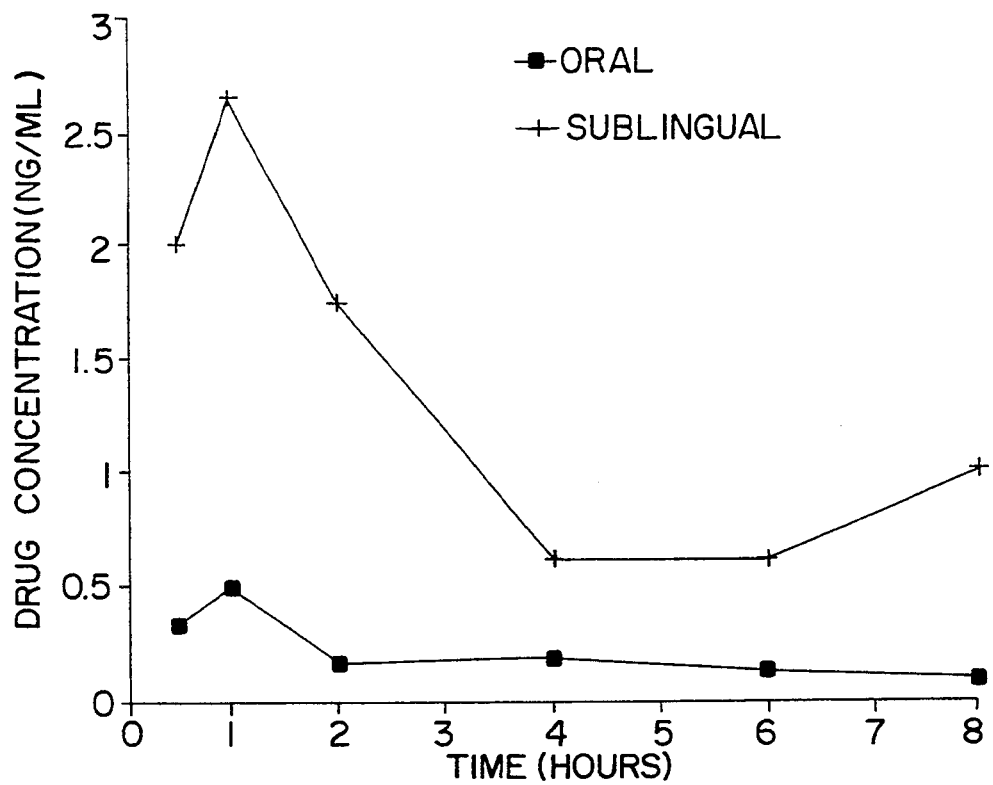
FIG. 9 is a graph illustrating the ratio of propoxyphene concentration to norpropoxyphene concentration for both per oral swallowed and sublingual administration in the subject seen in FIGS. 7 and 8.
Figure 10:
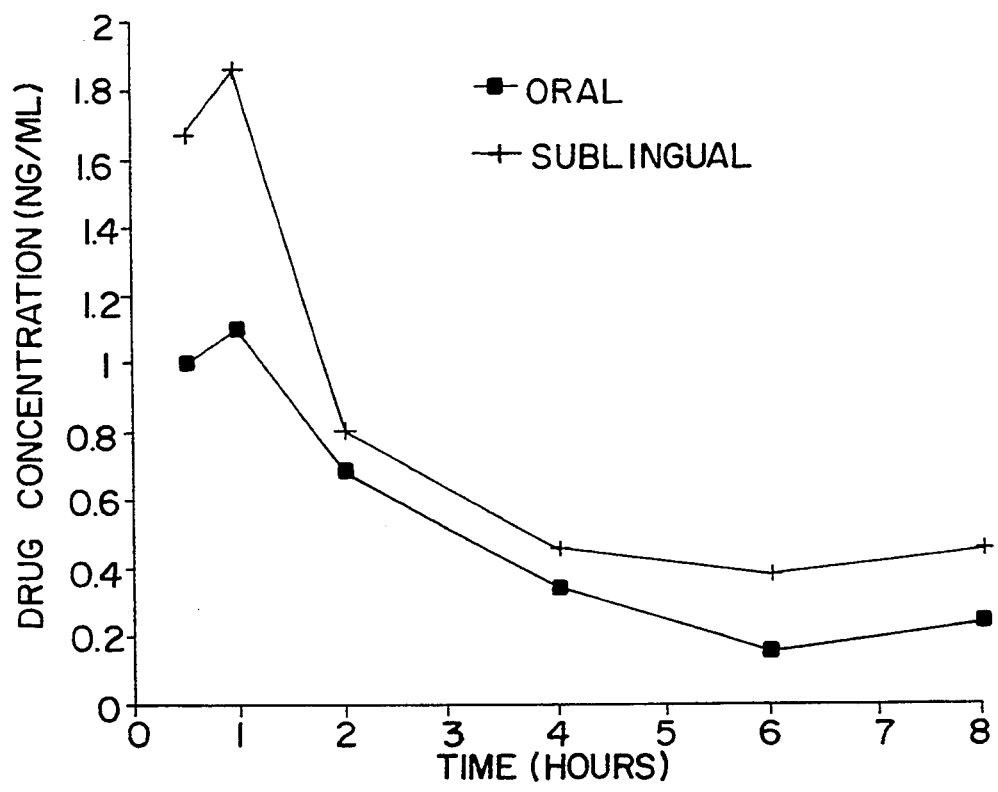
FIG. 10 is a graph illustrating the ratio of propoxyphene concentration to norpropoxyphene concentration for both per oral swallowed and sublingual administration in another subject in addition to that shown in FIGS. 7 and 8.

FIGS. 7 and 8 demonstrate the propoxyphene and norpropoxyphene plasma concentrations for (1) per oral swallowed and (2) sublingual administration in a single subject over an eight (8) hour period. FIG. 9 illustrates the propoxyphene/norpropoxyphene ratios for sublingual and oral dosing over time for the subject of FIGS. 7 and 8. FIG. 10 illustrates the same ratios for a second subject under the same test conditions. The increase in wanted parent compound to unwanted metabolite for sublingual dosing is readily apparent. Thus sublingual dosing reduces propoxyphene dealkylation metabolism thereby increasing the therapeutic toxic ratio.

As a further example, another drug that has N-dealkylation to an unwanted metabolite is chlorimipramine (CL) which is metabolized to demethylchlorimipramine (DMCL).

Chlorimipramine is a specific inhibitor of serotonin uptake which is a desired property in the treatment of obsessive compulsive disorders, whereas demethylchlorimipramine is a potent inhibitor of norepinephrine. Thus the DMCL metabolite which in many individuals accumulates to levels much greater than CL thus qualitatively changing the biochemical effect during treatment. In addition, the accumulation of DMCL poses additional potential toxicity from its cardiac conduction slowing properties similar to that of norproxyphene.

Applicants administered 25 mg of CL to normal subjects per orally and sublingually. In subjects who had a high dealkylation level, sublingual administration markedly reduced the unwanted metabolite DMCL thereby increasing the wanted parent compound CL to unwanted metabolite DMCL ratio. Other subjects did not demonstrate this effect. Therefore, the sublingual administration would be important only for certain individual patients who were shown to have unfavorable ratios.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method for administering propoxyphene compound to the human central nervous system wherein a therapeutically effective amount of said compound is sublingually or buccally administered to a human, the improvement comprising the steps of:

a. selecting a lipid soluble compound comprising (+)-α-4-(dimethylamino)-3-methyl-1,2-diphenyl-2-butanol propionate hydrochloride that (1) has one or more unwanted or adverse metabolites comprising norpropoxyphene that are increased by portal vein entry to the liver;

b. placing said compound in a suitable intraoral formulation; and c. intraorally administering a therapeutically effective amount of said intraoral formulation so as to bypass the portal vein entry to the liver and to thereby decrease the formation of the unwanted metabolites; wherein the ratio of propoxyphene to the unwanted metabolite norpropoxyphene made available to the central nervous system is increased; and this intraoral method over a period of one or more doses is utilized to achieve sustained high levels of the propoxyphene relative to the unwanted metabolite norpropoxyphene.

* * * * *